(12) United States Patent
Iyengar et al.

(10) Patent No.: US 11,261,146 B2
(45) Date of Patent: Mar. 1, 2022

(54) PREPARATION OF 2,3,3,3-TETRAFLUOROPROPENE AND INTERMEDIATES THEREOF

(71) Applicant: SRF LIMITED, Haryana Gurgaon (IN)

(72) Inventors: Sarathy Iyengar, Haryana Gurgaon (IN); Sridhar Jeyaraman, Haryana Gurgaon (IN); Karthic Natarajan, Haryana Gurgaon (IN); Nathan Rajamani, Haryana Gurgaon (IN); Rahul Saxena, Haryana Gurgaon (IN); Anurag Jain, Haryana Gurgaon (IN)

(73) Assignee: SRF LIMITED, Haryana Gurgaon (IN)

( * ) Notice: Subject to any disclaimer, the term of this patent is extended or adjusted under 35 U.S.C. 154(b) by 0 days.

(21) Appl. No.: 17/282,446

(22) PCT Filed: Oct. 3, 2019

(86) PCT No.: PCT/IB2019/058418
§ 371 (c)(1),
(2) Date: Apr. 2, 2021

(87) PCT Pub. No.: WO2020/070684
PCT Pub. Date: Apr. 9, 2020

(65) Prior Publication Data
US 2021/0380507 A1 Dec. 9, 2021

(30) Foreign Application Priority Data

Oct. 4, 2018 (IN) .............................. 201811037658
Oct. 4, 2018 (IN) .............................. 201811037659

(51) Int. Cl.
| | | |
|---|---|---|
| C07C 17/25 | (2006.01) |
| C07C 17/20 | (2006.01) |
| C07C 17/278 | (2006.01) |
| C07C 21/18 | (2006.01) |
| C07C 19/08 | (2006.01) |
| C07C 21/04 | (2006.01) |
| C07C 19/04 | (2006.01) |
| C07C 17/087 | (2006.01) |
| B01J 21/04 | (2006.01) |
| B01J 23/26 | (2006.01) |

(52) U.S. Cl.
CPC .............. *C07C 17/25* (2013.01); *B01J 21/04* (2013.01); *B01J 23/26* (2013.01); *C07C 17/087* (2013.01); *C07C 17/206* (2013.01); *C07C 17/278* (2013.01)

(58) Field of Classification Search
None
See application file for complete search history.

(56) References Cited

U.S. PATENT DOCUMENTS

2014/0012050 A1    1/2014  Smith et al.
2014/0121424 A1*   5/2014  Nose ..................... C07C 17/206
                                                                570/160

FOREIGN PATENT DOCUMENTS

CN         102001912 A   *  4/2011

OTHER PUBLICATIONS

Translation of CN 102001912A, Apr. 2011, pp. 1-7 (Year: 2011).*
International Search Report and Written Opinion for International Application No. PCT/IB2019/058418, dated Jan. 21, 2020.

* cited by examiner

*Primary Examiner* — Medhanit W Bahta
(74) *Attorney, Agent, or Firm* — Marshall, Gerstein & Borun LLP

(57) ABSTRACT

The present invention provides a process for preparation of 2,3,3,3-tetrafluoropropene and intermediates thereof. Owing to its low global warming potential and zero ozone depleting potential, it is been proposed as a replacement for existing chlorofluorocarbons and hydrofluorocarbons as refrigerant.

13 Claims, No Drawings

PREPARATION OF 2,3,3,3-TETRAFLUOROPROPENE AND INTERMEDIATES THEREOF

CROSS-REFERENCE TO RELATED APPLICATIONS

This is the United States national phase of International Application No. PCT/IB2019/058418, filed Oct. 3, 2019, which claims priority to India Patent Application No. 201811037658, filed Oct. 4, 2018, and India Patent Application No. 201811037659, filed on Oct. 4, 2018. The entire contents of each the foregoing applications are incorporated herein by reference in their entirety.

FIELD OF THE INVENTION

The present invention provides a process for preparation of 2,3,3,3-tetrafluoropropene and intermediates thereof.

BACKGROUND OF THE INVENTION 2,3,3,3-Tetrafluoropropene (HFO-1234yf) is a hydrofluoroolefin. Owing to its low global warming potential and zero ozone depleting potential, it is been proposed as a replacement for existing chlorofluorocarbon and hydrofluorocarbon refrigerants.

Several methods are known in the art for the synthesis of HFO-1234yf. e.g., U.S. Pat. No. 8,546,623 discloses a process for preparing 2,3,3,3-tetrafluoropropene by dehydrohalogenating 2-chloro-2,3,3,3 tetrafluoro propane using hydrogen fluoride in presence of a zinc/chromia catalyst at a temperature selected in the range of −70 to 400° C.

The inventors of the present invention found that 2,3,3,3-tetrafluoropropene can also be prepared from trichlorodifluoropropanes in presence of hydrogen fluoride and a co-precipitated chromia/alumina catalyst in a continuous manner.

Trichlorodifluoropropanes are important intermediates in the synthesis of various hydrofluoroolefins. These hydrofluoroolefins such as 2,3,3,3-tetrafluoropropene and 1,3,3,3-tetrafluoropropene find applications as refrigerants, cleaning agents, blowing agents, and solvents etc.

The inventors of the present invention provides an alternate process for 2,3,3,3-tetrafluoropropene using trichlorodifluoropropanes as intermediates

Object of the Invention

The object of the present invention is to provide a process for preparation of 2,3,3,3-tetrafluoropropene and intermediates thereof.

SUMMARY OF THE INVENTION

In first aspect, the present invention provides a process for preparation of 2,3,3,3-tetrafluoropropene,
comprising the steps of:
a) reacting carbon tetrachloride with ethylene in presence of a metallic catalyst and an organic ligand to obtain a reaction mixture 1 comprising 1,1,1,3-tetrachloropropane;
b) de-hydrohalogenating the reaction mixture 1 to obtain a reaction mixture 2, comprising trichloropropenes;
c) fluorinating the reaction mixture 2 to obtain a reaction mixture 3 comprising trichlorodifluoropropanes; and
d) simultaneous fluorination and de-hydrohalogenation of the reaction mixture 3 to obtain 2,3,3,3-tetrafluoropropene.

In second aspect, the present invention provides a process for preparation of 2,3,3,3-tetrafluoropropene,
comprising the steps of:
a) de-hydrohalogenating 1,1,1,3-tetrachloropropane to obtain a reaction mixture 2 comprising trichloropropenes;
b) fluorinating the reaction mixture 2 to obtain a reaction mixture 3 comprising trichlorodifluoropropanes; and
c) simultaneously fluorinating and de-hydrohalogenating the reaction mixture 3 to obtain 2,3,3,3-tetrafluoropropene.

In third aspect, the present invention provides a process for preparation of 2,3,3,3-tetrafluoropropene,
comprising the step of:
a) fluorinating a reaction mixture 2 comprising trichloropropenes to obtain a reaction mixture 3 comprising trichlorodifluoropropanes; and
b) simultaneously fluorinating and de-hydrohalogenating the reaction mixture 3 to obtain 2,3,3,3-tetrafluoropropene.

In fourth aspect, the present invention provides a process for preparation of 2,3,3,3-tetrafluoropropene, comprising a step of simultaneous fluorination and de-hydrohalogenation of a mixture comprising trichlorodifluoropropanes to obtain 2,3,3,3-tetrafluoropropene.

In fifth aspect, the present invention provides a process for preparation of a compound of Formula 1, $X^2CH_2CHFCCl_2X^1$, wherein $X^1$ and $X^2$ represents chlorine or fluorine; provided that $X^1$ is not same as $X^2$,
comprising the steps of:
a) reacting carbon tetrachloride with ethylene in presence of a metallic catalyst to obtain a reaction mixture 1 comprising 1,1,1,3-tetrachloropropane;
b) de-hydrohalogenating the reaction mixture 1 to obtain a reaction mixture 2, comprising trichloropropenes;
c) fluorinating the reaction mixture 2 to obtain the compound of formula 1.

In sixth aspect, the present invention provides a process for preparation of a compound of Formula 1, $X^2CH_2CHFCCl_2X^1$, wherein $X^1$ and $X^2$ represents chlorine or fluorine; provided that $X^1$ is not same as $X^2$,
comprising the steps of:
a) de-hydrohalogenating 1,1,1,3-tetrachloropropane to obtain a reaction mixture 2 comprising trichloropropenes;
b) fluorinating the reaction mixture 2 to obtain the compounds of formula 1.

In seventh aspect, the present invention provides a process for preparation of a compound of formula 1, $X^2CH_2CHFCCl_2X^1$, wherein $X^1$ and $X^2$ represents chlorine or fluorine; provided that $X^1$ is not same as $X^2$, comprising the step of fluorinating a mixture of 1,1,3-trichloroprop-1-ene and 3,3,3-trichloroprop-1-ene, to obtain the compounds of formula 1.

DETAILED DESCRIPTION OF THE INVENTION

As used herein, the "reaction mixture 1" comprises of 1,1,1,3-tetrachloropropane, ethylene and carbon tetrachloride.

As used herein, the "reaction mixture 2" comprises of 1,1,3-trichloroprop-1-ene and 3,3,3-trichloroprop-1-ene.

As used herein, the reaction mixture 3 comprises of mixture of trichlorodifluoropropanes.

As used herein, the "trichlorodifluoropropanes" refers to a mixture of 1,1,3-trichloro-1,2-difluoropropane and 1,1,1-trichloro-2,3-difluoropropane. The mixture of trichlorodifluoropropanes comprises of 0 to 100% w/w of 1,1,3-trichloro-1,2-difluoropropane and 100 to 0% w/w of 1,1,1-trichloro-2,3-difluoropropane respectively.

As used herein, the term "metallic catalyst" refers to elemental powders, salts, and organometallic compounds of the transition metals. The preferred metallic catalysts include copper and iron. Exemplary cuprous salts and organometallic cuprous compounds include, without limitation, cuprous chloride, cuprous bromide, cuprous cyanide, cuprous sulfate, and cuprous phenyl. Exemplary iron salts and organometallic ferrous compounds include, without limitation, ferrous chloride, ferric chloride, Tris (2,2'-bipyridine) iron (II) hexafluorophosphate. Exemplary copper and iron powders preferably are fine, substantially pure powders having a particle size no greater than about 100 mesh, and preferably no greater than about 325 mesh. The more preferred metallic catalysts include cuprous chloride and iron powder.

As used herein, the term "The organic ligand" refers to the compound capable of forming a complex with a metallic catalyst having the properties and attributes as described above. Suitable organic ligands include amines, nitrites, amides, and phosphates. Examples of preferred nitrites include, for example, acetonitrile, pentanenitrile, benzonitrile, and tolunitriles. Examples of preferred amides, for example, N-ethylacetamide, acetanilide, aceto-p-toluidide, and hexamethlyenephosphomamide. Examples of preferred phosphates include, for example, trimethylphosphate, triethylphosphate, tributylphosphate, and triphenylphosphate.

In a particular embodiment, the reaction between ethylene and carbon tetrachloride is carried out in presence of metallic catalyst and a phosphate ligand to produce 1,1,1,3-tetrachloropropane.

As used herein, the step of de-hydrohalogenating involves eliminating hydrogen chloride from tetrachloropropane to produce trichloropropene.

In an embodiment, the step of de-hydrohalogenation is carried out using a base in presence of a phase transfer catalyst.

Examples of base include an organic or an inorganic base or the mixtures thereof. Examples of inorganic base includes alkali metal hydroxides selected from lithium hydroxide, sodium hydroxide, potassium hydroxide and alkaline earth metal hydroxides selected from calcium hydroxide and magnesium hydroxide. The organic bases are selected from the group consisting of alkali metal alkoxides, and the like. Examples of alkali metal alkoxide includes sodium methoxide, sodium ethoxide, sodium propoxide, sodium isopropoxide, sodium butoxide, sodium tertiary butoxide or potassium methoxide, potassium ethoxide, potassium propoxide, potassium isopropoxide, potassium butoxide, potassium tertiary butoxide and the like.

Examples of phase transfer catalyst include crown ethers; cryptates; polyalkylene glycols or derivatives thereof; and onium salts. Examples of crown ethers includes 18-crown-6 and 15-crown-5. Examples of polyalkylene glycol includes polyethylene glycol and polypropylene glycol. Examples of onium salts includes benzyltriethylammonium chloride, methyltrioctylammonium chloride, tetra-nbutylammonium chloride, tetra-n-butylammonium bromide, tetranbutylphosphonium chloride, bis [tris(dimethylamino) phosphine] iminium chloride, tetratris [tris(dimethylamino) phosphinimino] phosphonium chloride, and trioctylmethyl ammonium hydrogen sulfate.

In another embodiment, the step of de-hydrohalogenation is performed using a base in a non-aqueous, non-alcohol solvent that is at least essentially miscible with the halopropane, wherein the reaction is performed at a temperature at which de-hydrohalogenation will occur and wherein de-hydrohalogenation is carried out with or without a phase transfer catalyst.

In another embodiment, the step of de-hydrohalogenation is performed thermally at a temperature of 35° C. to 400° C.

The phase transfer catalyst is used in 0.1 to 10 mole percentage. The phase transfer catalyst of the present invention can be easily recovered and reused.

In a particular embodiment, 1,1,1,3-tetrachloropropane is de-hydrohalogenated using a base in presence of a phase transfer catalyst at a temperature of 15° C. to 45° C. to give a mixture of 1,1,3-trichloroprop-1-ene and 3,3,3-trichloroprop-1-lene.

As used herein, the term "fluorinating" refers to reacting with a fluorinating agent in hydrogen fluoride as a solvent.

Fluorinating agent is fluorine gas, optionally provided as fluorinating gaseous composition comprising fluorine and optionally one or more carrier gases (e.g. nitrogen or helium). Any carrier gases are suitably inert gases, suitably inert to fluorine and suitably also inert to any other starting materials, products, or reagents of the methods of the invention.

The fluorination reaction of the present invention is preferably carried out in a Hastelloy pressure reactor. The reactor is first passivated using a mixture of 8-12% of fluorine in nitrogen. The passivation of the reactor aids in fluorination reaction and it prevent corrosion of reactor and provides a safe process because sometimes explosion also possible with non-passivated metal surface with high flow rate.

The fluorinating agent is added at a flow rate of 40-110 cc/minute.

In a particular embodiment, the fluorinating gaseous composition comprises or consists essentially of 5 to 15% fluorine and 85 to 95% nitrogen, most suitably 10% fluorine and 90% nitrogen.

Fluorinating gaseous composition is suitably provided to a reaction mixture as a constant flow.

The fluorination reaction is carried out in hydrofluoric acid as a solvent. Preferably anhydrous hydrofluoric acid is used as a solvent and 6 to 10 moles of anhydrous hydrofluoric acid are preferred. The mixture is fed at a flow rate of 3-7 g/hr.

In a particular embodiment, the fluorination is carried out using a gaseous composition comprising fluorine and nitrogen in hydrogen fluoride solvent.

The fluorination is carried out at a temperature range of −40 to −70° C. at a pressure of 0 to 0.5 kg/cm$^2$.

In a particular embodiment, a mixture of 1,1,3-trichloroprop-1-ene and 3,3,3-trichloroprop-1-lene is fluorinated using a fluorinating gaseous composition comprises of 5 to 15% fluorine and 85 to 95% nitrogen in hydrogen fluoride solvent, to give a mixture of 1,1,3-trichloro-1,2-difluoropropane and 1,1,1-trichloro-2,3-difluoropropane.

In an embodiment, the fluorination gives a mixture of trichlorodifluoroproanes wherein, 1,1,3-trichloro-1,2-difluoropropane is present in an amount not less than 40% w/w of the total concentration of mixture of trichlorodifluoroproanes.

The mixture of trichlorodifluoroproanes is isolated by any method known in the art, for example, chemical separation, extraction, acid-base neutralization, distillation, evaporation, column chromatography and filtration or a mixture thereof.

In another embodiment, the mixture of trichlorodifluoroproanes is separated by distillation.

The preferred means of isolation is quenching followed by distillation.

The distillation is performed at a pressure selected in the range of 5 torr to 15 torr and at a temperature selected in the range of 20° C. to 30° C.

After completion of reaction, 80 to 90% of anhydrous hydrofluoric acid is recovered while the remaining is quenched using a base selected from a group consisting of sodium bicarbonate, sodium carbonate, potassium bicarbonate, potassium carbonate and aqueous ammonia.

In a particular embodiment, 1,1,3-trichloroprop-1-ene is fluorinated using a fluorinating gaseous composition comprises of 5 to 15% fluorine and 85 to 95% nitrogen in hydrogen fluoride solvent, to give 1,1,3-trichloro-1,2-difluoropropane.

In a particular embodiment, 3,3,3-trichloroprop-1-lene is fluorinated using a fluorinating gaseous composition comprises of 5 to 15% fluorine and 85 to 95% nitrogen in hydrogen fluoride solvent, to give 1,1,1-trichloro-2,3-difluoropropane.

The mixture of trichlorodifluoropropanes as prepared by process of the present invention can be isolated or can be used as such without isolation for the preparation of hydrofluoro olefins.

As used herein, the step of "simultaneous fluorination and de-hydrohalogenation" is carried out by using hydrogen fluoride in the presence of co-precipitated chromia-alumina catalyst.

The hydrogen fluoride is essentially anhydrous hydrogen fluoride. The molar ratio of trichlorodifluoropropane to hydrogen fluoride is selected in the range of 1:4 to 1:20.

The step of simultaneous fluorination and de-hydrohalogenation is performed at a temperature of temperature of 35° C. to 400° C. at an atmospheric pressure. The step of simultaneous fluorination and de-hydrohalogenation is preferably performed at a temperature of 100° C. to 300° C. and most preferably at a temperature of 200° C. to 250° C.

As used herein, the co-precipitated chromia-alumina catalyst is essentially amorphous. The co-precipitated chromia/alumina catalyst used in the present invention may attain some degree of crystallinity over a period of time at high temperature.

In another embodiment of the present invention, the co-precipitated chromia/alumina catalyst is impregnated with zinc, nickel, magnesium or salts thereof.

In another embodiment of the present invention, the co-precipitated chromia/alumina catalyst is impregnated with zinc chloride.

In another embodiment of the present invention, the process of co-precipitation is performed using a base selected from ammonium hydroxide, sodium hydroxide and potassium hydroxide.

In another embodiment of the present invention, the co-precipitated chromia/alumina catalyst contain chromium-aluminium in the atomic ratio of 1:1 to 1:14 and the amount of zinc compound impregnated ranges from about 2% to about 12%.

In another embodiment of the present invention, the co-precipitated chromia/alumina catalyst contains about 20% to about 25% of chromia, about 70% to about 75% of alumina and about 4% to about 6% of zinc chloride.

In another embodiment of the present invention, the co-precipitated chromia/alumina catalyst contains about 22% to about 24% of chromia, about 71% to about 73% of alumina and about 4% to about 6% of zinc chloride.

In another embodiment of the present invention, the co-precipitated chromia/alumina catalyst has loss on ignition (LOI) of less than 20% at a maximum temperature of 375° C.

In another embodiment of the present invention, the co-precipitated chromia/alumina catalyst has crush strength of more than 5 Kg/cm$^2$.

In another embodiment of the present invention, the co-precipitated chromia/alumina catalyst has surface area of about 160 to about 300 m$^2$/g before it is subjected to pre-treatment with hydrogen fluoride.

In another embodiment of the present invention, the co-precipitated chromia/alumina catalyst has surface area of at least 250 m$^2$/g before it is subjected to pre-treatment with hydrogen fluoride.

In another embodiment of the present invention, the co-precipitated chromia/alumina catalyst has bulk density ranging from about 0.8 to about 0.95 Kg/l.

In another embodiment of the present invention, the chromia/alumina catalyst is in the form of pellets, granules or sticks of appropriate size for use in fixed bed or fluidised bed. The catalyst may be supported or unsupported.

In a preferred embodiment of the present invention, the chromia/alumina catalyst is present as a fixed bed.

In another embodiment, the mixture of trichlorodifluoropropanes are used as such for preparation of 2,3,3,3-tetrafluoropropene (1234yf) and 1,1,1,3-etetrafluoropropene (1234ze).

As used herein, the term "catalyst" refers to the metallic catalysts and organic ligands that form suitable catalyst complexes.

In another embodiment, the step of de-hydrohalogenation is performed thermally at a temperature of 35° C. to 400° C.

The compound of Formula I is isolated by any method known in the art, for example, chemical separation, extraction, acid-base neutralization, distillation, evaporation, column chromatography and filtration or a mixture thereof.

The compounds of formula 1 as prepared by process of the present invention can be isolated or can be used as such without isolation for the preparation of hydrofluoro olefins.

The completion of the reaction may be monitored by any one of chromatographic techniques such as thin layer chromatography (TLC), high pressure liquid chromatography (HPLC), ultra-pressure liquid chromatography (UPLC), Gas chromatography (GC), liquid chromatography (LC) and alike.

Unless stated to the contrary, any of the words "comprising", "comprises" and includes mean "including without limitation" and shall not be construed to limit any general statement that it follows to the specific or similar items or matters immediately following it.

Embodiments of the invention are not mutually exclusive, but may be implemented in various combinations. The described embodiments of the invention and the disclosed examples are given for the purpose of illustration rather than limitation of the invention as set forth in the appended claims.

The following example is given by way of illustration and therefore should not be construed to limit the scope of the present invention.

EXAMPLES

Example 1: Preparation of 1,1,1,3-tetrachloropropane

Carbon tetrachloride (8.452 mol), Triethylphosphate (0.631 mol), Iron (0.278 mol), Iron chloride (0.4 g) was charged in Hastalloy pressure reactor. Then the reaction mass was flushed with nitrogen gas at the rate of 2 Kg/cm$^2$ for two times and Ethylene was flushed at the rate of 2 Kg/cm$^2$. After that rector has been pressurized with 4 Kg/cm$^2$ of ethylene, the reaction mixture was gradually heated to a temperature of 90° C. and subsequently raised to 120° C. Ethylene pressure was dropped when temperature reaches 120° C. The ethylene pressure was then maintained at the rate of 8 Kg/cm$^2$. After 12 hours reaction was stopped and unreacted ethylene was vented and recycled back to the reactor, the reaction mass was unloaded and taken for distillation. Distillation done under vacuum. Initially unreacted carbon tetrachloride was collected and recycled, then product cut 1185 g was collected, the residue used for next reaction as catalyst (recycle the catalyst).
Purity: >98% by GC (Area %)
Yield: 77%

Example 2: Preparation of 1,1,1,3-tetrachloropropane

Carbon tetrachloride (8.452 mol), tributylphosphate (0.631 mol), Iron (0.278 mol), Iron chloride (0.4 g) was charged in Hastalloy pressure reactor. Then the reaction mass was flushed with nitrogen gas at the rate of 2 Kg/cm$^2$ for two times and Ethylene was flushed at the rate of 2 Kg/cm$^2$. After that rector has been pressurized with 4 Kg/cm$^2$ of ethylene, the reaction mixture was gradually heated to a temperature of 90° C. and subsequently raised to 120° C. Ethylene pressure was dropped when temperature reaches 120° C. The ethylene pressure was then maintained at the rate of 8 Kg/cm$^2$. After 12 hours reaction was stopped and unreacted ethylene was vented and recycled back to the reactor, the reaction mass was unloaded and taken for distillation. Distillation done under vacuum. Initially unreacted carbon tetrachloride was collected and recycled, then product cut 1185 g was collected, the residue used for next reaction as catalyst (recycle the catalyst).
Purity: >98% by GC (Area %)
Yield: 78%

Example 3: Preparation of 1,1,1,3-tetrachloropropane

Carbon tetrachloride (8.452 mol), trimethylphosphate (0.631 mol), Iron (0.278 mol), Iron chloride (0.4 g) was charged in Hastalloy pressure reactor. Then the reaction mass was flushed with nitrogen gas at the rate of 2 Kg/cm$^2$ for two times and Ethylene was flushed at the rate of 2 Kg/cm$^2$. After that rector has been pressurized with 4 Kg/cm$^2$ of ethylene, the reaction mixture was gradually heated to a temperature of 90° C. and subsequently raised to 120° C. Ethylene pressure was dropped when temperature reaches 120° C. The ethylene pressure was then maintained at the rate of 8 Kg/cm$^2$. After 12 hours reaction was stopped and unreacted ethylene was vented and recycled back to the reactor, the reaction mass was unloaded and taken for distillation. Distillation done under vacuum. Initially unreacted carbon tetrachloride was collected and recycled, then product cut 1185 g was collected, the residue used for next reaction as catalyst (recycle the catalyst).
Purity: >98% by GC (Area %)
Yield: 75%

Example 4: Preparation of Trichloropropene 1,1,1,3-Tetrachloropropane (3.33 mol) and methyltrioctylammonium chloride (0.0495 mol) was charged into the glass reactor at 32° C. and 1 atm. An aqueous solution of sodium hydroxide (20%; 4 mol) was added into the reaction mass drop-wise at 32 to 35° C. with agitation for 5 hours. After completion of addition, the reaction mixture was allowed to stir for 12 hours at 32° C. The reaction mass was unloaded and taken for distillation. Distillation done at reduced pressure. Initially low boiling impurities were separated and then 385 grams of product was collected.
Purity: >98%
Yield: 80%

Example 5: Preparation of Trichloropropene 1,1,1,3-Tetrachloropropane (3.33 mol) and tetra-n-butylammonium bromide (0.05 mol) was charged into the glass reactor at 32° C. and 1 atm. An aqueous solution of sodium hydroxide (20%; 4 mol) was added into the reaction mass drop-wise at 32 to 35° C. with agitation for 5 hours. After completion of addition, the reaction mixture was allowed to stir for 12 hours at 32° C. The reaction mass was unloaded and taken for distillation. Distillation done at reduced pressure. Initially low boiling impurities were separated and then 385 grams of product was collected.
Purity: >98%
Yield: 83%

Example 6: Preparation of Trichloropropene 1,1,1,3-Tetrachloropropane (3.33 mol) and tetranbutylphosphonium chloride (0.05 mol) was charged into the glass reactor at 32° C. and 1 atm. An aqueous solution of sodium hydroxide (20%; 4 mol) was added into the reaction mass drop-wise at 32 to 35° C. with agitation for 5 hours. After completion of addition, the reaction mixture was allowed to stir for 12 hours at 32° C. The reaction mass was unloaded and taken for distillation. Distillation done at reduced pressure. Initially low boiling impurities were separated and then 385 grams of product was collected.
Purity: >98%
Yield: 82%

Example 7: Preparation of a Mixture of Trichlorodifluoropropane

Hastelloy pressure reactor was passivated using 10% F$_2$/N$_2$ mixture. The reactor was cooled to a temperature of −80° C. and vacuumized. The pressure reactor was then charged with anhydrous hydrofluoric acid (6.5 mol) at a temperature of −80° C. to −40° C. The reactor was cooled to −60° C. and 0.4722 moles a mixture of 1,1,3 trichloropropene (formula 2a) and 3,3,3 trichloropropene (formula 2b) were fed through one dip tube with the flow of 7 g/hour and 20% F$_2$/N$_2$ mixture (0.6053 mol) was purged through another dip tube as with the flow of 100 cc/minute at −60° C. and 1 atm pressure simultaneously. After completion of reaction, anhydrous hydrofluoric acid (100 g) was recovered and 85 g crude product was unloaded with residual hydrofluoric acid. Then residual hydrofluoric acid was quenched using saturated potassium bicarbonate at 20° C. and taken for boil off to get moisture free product (74 g).
Purity (by GC): 95%
Yield: 70%

Comparative Example 1: Preparation of a Mixture of Trichlorodifluoropropane

Hastelloy pressure reactor was passivated using 10% $F_2/N_2$ mixture. The reactor was cooled to a temperature of −80° C. and vacuumized. The reactor was cooled to −60° C. and 0.4722 moles a mixture of 1,1,3 trichloropropene (formula 2a) and 3,3,3 trichloropropene (formula 2b) were fed through one dip tube with the flow of 7 g/hour and 20% $F_2/N_2$ mixture (0.6053 mol) was purged through another dip tube as with the flow of 100 cc/minute at −60° C. and 1 atm pressure simultaneously. After completion of reaction, crude product was unloaded and was quenched using saturated potassium bicarbonate at 20° C. and taken for boil off to get moisture free product.
Purity (by GC): 80%
Yield: 55%

Example 8: Preparation of 2,3,3,3-tetrafluoropropene

Moisture was removed from Chromia-Alumina-Zinc catalyst by passing nitrogen with the flow of 50 cc/minute at 250° C. and 1 atm for 24 hours. Then vapour phase catalyst (Chromia-Alumina-Zinc) was activated by passing anhydrous hydrofluoric acid at 310° C. and 1 atm with the flow of 2 grams/minute. After activation of catalyst, Isomers of Trichlorodifluoropropane passed with the flow of 1 gram/minute and anhydrous hydrofluoric acid passed with flow of 2 grams/minute through different points of vapour phase reactor at 220 to 250° C. and 1 atm. outlet of reactor was connected with scrubber set-up (it contains 40% KOH solution) and product was collected from the outlet of scrubber.

We claim:

1. A process for preparation of 2,3,3,3-tetrafluoropropene, comprising the steps of:
    a) reacting carbon tetrachloride with ethylene in presence of a metallic catalyst and an organic ligand to obtain a reaction mixture 1, comprising 1,1,1,3-tetrachloropropane;
    b) de-hydrohalogenating the reaction mixture 1 to obtain a reaction mixture 2 comprising 1,1,3-trichloroprop-1-ene and 3,3,3-trichloroprop-1-ene;
    c) fluorinating the reaction mixture 2 using a gaseous composition of fluorine and nitrogen in the presence of anhydrous hydrogen fluoride to obtain a reaction mixture 3, comprising trichlorodifluoropropanes of formula 1, $X^2CH_2CHFCCl_2X^1$, wherein $X^1$ and $X^2$ represents chlorine or fluorine; provided that $X^1$ is not same as $X^2$; and
    d) simultaneous fluorination and de-hydrohalogenation of the reaction mixture 3 to obtain 2,3,3,3-tetrafluoropropene.

2. A process for preparation of 2,3,3,3-tetrafluoropropene, comprising the steps of:
    a) de-hydrohalogenating 1,1,1,3-tetrachloropropane to obtain a reaction mixture 2, comprising 1,1,3-trichloroprop-1-ene and 3,3,3-trichloroprop-1-ene;
    b) fluorinating the reaction mixture 2 using a gaseous composition of fluorine and nitrogen in the presence of anhydrous hydrogen fluoride to obtain a reaction mixture 3, comprising trichlorodifluoropropanes of formula 1, $X^2CH_2CHFCCl_2X^1$, wherein $X^1$ and $X^2$ represents chlorine or fluorine; provided that $X^1$ is not same as $X^2$; and
    c) simultaneous fluorination and de-hydrohalogenation of the reaction mixture 3 to obtain 2,3,3,3-tetrafluoropropene.

3. A process for preparation of 2,3,3,3-tetrafluoropropene, comprising the step of:
    a) fluorinating a reaction mixture comprising 1,1,3-trichloroprop-1-ene and 3,3,3-trichloroprop-1-ene using a gaseous corn position of fluorine and nitrogen in the presence of anhydrous hydrogen fluoride, to obtain a reaction mixture 3, comprising trichlorodifluoropropanes of formula 1, $X^2CH_2CHFCCl_2X^1$, wherein $X^1$ and $X^2$ represents chlorine or fluorine; provided that $X^1$ is not same as $X^2$; and
    b) simultaneous fluorination and de-hydrohalogenation of the reaction mixture 3 to obtain 2,3,3,3-tetrafluoropropene.

4. A process for preparation of 2,3,3,3-tetrafluoropropene, comprising a step of simultaneously fluorination and de-hydrohalogenation of a mixture comprising trichlorodifluoropropanes of formula 1, $X^2CH_2CHFCCl_2X^1$, wherein $X^1$ and $X^2$ represents chlorine or fluorine; provided that $X^1$ is not same as $X^2$; to obtain 2,3,3,3-tetrafluoropropene.

5. A process for preparation of trichlorodifluoropropanes of formula 1, $X^2CH_2CHFCCl_2X^1$, wherein $X^1$ and $X^2$ represents chlorine or fluorine; provided that $X^1$ is not same as $X^2$, comprising the steps of:
    a) reacting carbon tetrachloride with ethylene in presence of a metallic catalyst to obtain a reaction mixture 1, comprising 1,1,1,3-tetrachloropropane;
    b) de-hydrohalogenating the reaction mixture 1 to obtain a reaction mixture 2, comprising 1,1,3-trichloroprop-1-ene and 3,3,3-trichloroprop-1-ene;
    c) fluorinating the reaction mixture 2 using a gaseous composition of fluorine and nitrogen in the presence of anhydrous hydrogen fluoride, to obtain a compound of formula 1.

6. A process for preparation of trichlorodifluoropropanes of formula 1, $X^2CH_2CHFCCl_2X^1$, wherein $X^1$ and $X^2$ represents chlorine or fluorine; provided that $X^1$ is not same as $X^2$, comprising the steps of:
    a) de-hydrohalogenating 1,1,1,3-tetrachloropropane to obtain a reaction mixture 2, comprising 1,1,3-trichloroprop-1-ene and 3,3,3-trichloroprop-1-ene;
    b) fluorinating the reaction mixture 2 using a gaseous composition of fluorine and nitrogen in the presence of anhydrous hydrogen fluoride, to obtain a compound of formula 1.

7. A process for preparation of trichlorodifluoropropanes of formula 1, $X^2CH_2CHFCCl_2X^1$, wherein $X^1$ and $X^2$ represents chlorine or fluorine; provided that $X^1$ is not same as $X^2$, comprising the steps of, fluorinating a mixture comprising 1,1,3-trichloroprop-1-ene and 3,3,3-trichloroprop-1-ene using a gaseous composition of fluorine and nitrogen in the presence of anhydrous hydrogen fluoride to obtain a compound of formula 1.

8. The process as claimed in claim 1, wherein the metallic catalyst is selected from a group consisting of cuprous chloride, cuprous bromide, cuprous cyanide, cuprous sulfate, ferrous chloride, ferric chloride and tris (2,2'-bipyridine) iron (II) hexafluorophosphate.

9. The process as claimed in claim 1, wherein the organic ligand is selected from a group consisting of trimethylphosphate, triethylphosphate, tributylphosphate, and triphenylphosphate.

10. The process as claimed in claim 1, wherein the step of de-hydrohalogenation is carried out using a base in the presence of a phase transfer catalyst.

11. The process as claimed in claim 10, wherein the base is selected from a group consisting of sodium hydroxide or potassium hydroxide.

12. The process as claimed in claim 10, wherein the phase transfer catalyst is selected from a group consisting of crown ethers, polyalkylene glycols, benzyltriethylammonium chloride, methyltrioctylammonium chloride, tetra-nbutylammonium chloride, tetra-n-butylammonium bromide, tetranbutylphosphonium chloride, bis [tris(dimethylamino) phosphine] iminium chloride, tetratris [tris(dimethylamino) phosphinimino] phosphonium chloride, and trioctylmethyl ammonium hydrogen sulfate.

13. The process as claimed in claim 1, wherein the step of simultaneous fluorination and de-hydrohalogenation is carried out by using hydrogen fluoride in the presence of co-precipitated chromia-alumina catalyst.

\* \* \* \* \*